US008099301B2

(12) United States Patent
Keresman, III et al.

(10) Patent No.: US 8,099,301 B2
(45) Date of Patent: Jan. 17, 2012

(54) SECURE ON-LINE AUTHENTICATION SYSTEM FOR PROCESSING PRESCRIPTION DRUG FULFILLMENT

(75) Inventors: Michael A. Keresman, III, Kirtland Hills, OH (US); Jeffry J. Bowman, Willoughby Hills, OH (US); Francis M. Sherwin, Cleveland Heights, OH (US); Chandra S. Balasubramanian, Mentor-on-the-Lake, OH (US); Ravishankar S. Bhagavatula, Yorba Linda, CA (US)

(73) Assignee: Cardinalcommerce Corporation, Mentor, OH (US)

( * ) Notice: Subject to any disclaimer, the term of this patent is extended or adjusted under 35 U.S.C. 154(b) by 0 days.

(21) Appl. No.: 12/952,680

(22) Filed: Nov. 23, 2010

(65) Prior Publication Data

US 2011/0071847 A1    Mar. 24, 2011

Related U.S. Application Data

(63) Continuation of application No. 09/799,650, filed on Mar. 6, 2001, now abandoned.

(60) Provisional application No. 60/187,341, filed on Mar. 6, 2000.

(51) Int. Cl.
*G06Q 10/00* (2012.01)

(52) U.S. Cl. .............................................. 705/2; 705/3
(58) Field of Classification Search .................. 705/2, 3
See application file for complete search history.

(56) References Cited

U.S. PATENT DOCUMENTS

| 5,297,189 | A | 3/1994 | Chabemaud |
| 5,867,821 | A | 2/1999 | Ballantyne et al. |
| 5,889,942 | A | 3/1999 | Orenshteyn |
| 5,943,423 | A | 8/1999 | Muftic |
| 6,283,322 | B1 | 9/2001 | Liff et al. |
| 6,363,485 | B1 | 3/2002 | Adams et al. |
| 2002/0052762 | A1* | 5/2002 | Kobylevsky et al. ............. 705/2 |
| 2002/0062228 | A1* | 5/2002 | Portnoy et al. .................... 705/3 |

* cited by examiner

*Primary Examiner* — Robert Morgan
*Assistant Examiner* — Maroun Kanaan
(74) *Attorney, Agent, or Firm* — Fay Sharpe LLP

(57) ABSTRACT

A method of processing drug prescriptions via a communications network includes registering doctors, pharmacies and patients as participants such that each registered participant's identity is uniquely defined and determinable. Registered doctors from which prescriptions are received via the communications network have their identities authenticated. Each of the received prescriptions indicates a respective registered patient's identity for whom the prescription is intended. Registered patients from which orders are received via the communications network also have their identities authenticated. Each of the received orders indicates the prescription being ordered. The method also includes forwarding the orders to registered pharmacies via the communications network.

27 Claims, 5 Drawing Sheets

SECURE ON-LINE AUTHENTICATION SYSTEM FOR PROCESSING PRESCRIPTION DRUG FULFILLMENT

This application is a continuation of U.S. patent application Ser. No. 09/799,650, filed on Mar. 6, 2001, now abandoned which claims the benefit of U.S. Provisional Application No. 60/187,341 filed Mar. 6, 2000.

BACKGROUND OF THE INVENTION

The present invention relates to the art of Internet security and the authentication of otherwise unknown persons. It finds particular application in conjunction with Internet based fulfillment of prescription drug orders and/or access to confidential pharmaceutical or medical records. Consequently, it will be described with particular reference thereto. However, it is to be appreciated that the present invention is also amenable to other like applications.

The Internet is an electronic communications network useful for transferring data or information. Due to its speed and convenience, many individuals and businesses find it advantageous to communicate, exchange data and/or conduct transactions over the Internet. It is desired, e.g., in the medical and pharmaceutical fields, to have a patient's medical or pharmaceutical records readily accessible to doctors and/or pharmacies over the Internet. In this manner, physicians and/or pharmacists may make informed treatment/prescription decisions based on the particular circumstance of the patient (e.g., the patient health, medical history, other drugs being taken or already prescribed, drug allergies, etc.). Additionally, patients may desire to have prescriptions conveniently filled over the Internet. The foregoing propositions, however, present certain difficulties which heretofore have not been sufficiently addressed.

Patient's typically wish to regulate access to sensitive or confidential information, such as medical and pharmaceutical record. Moreover, it advantageous to ensure that prescription drugs are not abused. That is to say, prescription drug fulfillment should be carefully administered so that only the patient for whom the drugs are intended actually receive the drugs, and that they only receive those drugs that are properly prescribed. Consequently, it is advantageous to have a suitable degree of security which prevents unauthorized access to a patient's confidential medical and pharmaceutical records, which prevents unauthorized individual from writing prescriptions, which prevents unauthorized individuals from receiving prescription drugs not meant for them, which prevents pharmacies from filling prescriptions improperly written or order, etc. The Internet is, however, an unsecure network vulnerable to potential mischief and/or fraud, e.g., via an individual's misrepresentation of their true identity. As Internet transactions are not carried out face-to-face, traditional authentication protocols (e.g., visual inspection of the individual, inspect of the individuals signature, direct review of the individuals credentials, etc.) tend to be ineffective or not applicable. Accordingly, there is desired, for use in connection with the Internet or other like communications networks, a processing system and/or technique that provides an appropriate level of security which guards against fraudulent or otherwise unauthorized prescription drug fulfillment transactions and/or unauthorized access to confidential medical and/or pharmaceutical records.

Complicating matters further is that fact that often a patient's medical and/or pharmaceutical records are maintained by multiple medical care givers or pharmaceutical prescription fillers. Previously developed security measures in this respect tend to be limited. For example, many record holders (e.g., medical or pharmaceutical facilities) have separate disparate security measures and/or authentication protocols. This is inconvenient and unduly repetitive for those which desire access to confidential records from a plurality of distinct record holders. A multitude of disparate protocols and security measures results in the users having to maintain numerous distinct passwords, IDs, electronic keys and/or other security software or devices, often, a different one for each record holder. Moreover, some record holders may use four character passwords which are capitalization sensitive while others may use eight character passwords which are capitalization independent. There is no standard authentication protocol among the various record holders having a presence on the Internet. This makes keeping track of the various protocols and remembering the various security passwords and IDs even more difficult for users. Additionally, the various record holders are each separately authenticating users' identities. This is unduly repetitive and inefficient, especially considering that the record holders' core competency is not likely to include identity authentication.

Commonly, the prescription drug fulfillment process or access to medical/pharmaceutical records involves a three party transaction. For example, typical prescription drug processing involves a doctor writing a prescription, a patient ordering the prescription and a pharmacy filling the prescription. As opposed to a "linear" two party transaction which is relatively simple (e.g., a commercial purchase/sale transaction), it can be problematic to coordinated transactions among three parties while maintaining appropriate security safeguards. Furthermore, in traditional prescription drug processing, the doctor often calls in a prescription to a particular pharmacy in order to expedite processing. This in turn locked the patient into using that pharmacy to fill the prescription, which may be undesired by patient for what ever reason (e.g., the patient may want to shop around for the best price before deciding which pharmacy to use). Even if the patient originally tells the doctor what pharmacy to use at the time the prescription is being written, the patient may later change their mind when the prescription is being ordered. Traditional prescription processing is unable to suitably accommodate a patient's desire to freely select a pharmacy after the prescription has been written, at best, filling of the prescription would be delayed or the process further complicated. For example, the doctor may have to be contacted by the patient, and may have to call in changes to both the original pharmacy where the prescription was called in and to the new pharmacy where the patient wishes to have the prescription filled.

The present invention contemplates a new and improved communications network processing system and technique for prescription drug fulfillment and/or regulating access to confidential medical/pharmaceutical records that overcomes the above-referenced problems and others.

SUMMARY OF THE INVENTION

In accordance with one aspect of the present invention, a method is provided. The method includes registering doctors, pharmacies and patients as participants such that each registered participant's identity is uniquely defined and determinable. Registered doctors from which prescriptions are received via the communications network have their identities authenticated. Each of the received prescriptions indicates a respective registered patient's identity for whom the prescription is intended. Registered patients from which orders are received via the communications network also have their identities authenticated. Each of the received orders indicates the prescription being ordered. The method also includes forwarding the orders to registered pharmacies via the communications network.

In accordance with a more limited aspect of the present invention, the method further includes receiving, via the communications network, confirmation from pharmacies to which orders were forwarded. Each of the confirmations indicates that at least one of the following has occurred: the pharmacy has received the order, the pharmacy has accepted the order, the pharmacy is filling the order or the pharmacy has completed filling the order.

In accordance with a more limited aspect of the present invention, the method further includes forwarding, via the communications network, the received confirmations to at least one of the patient from which the corresponding order was received and the doctor from which the correspond prescription was received.

In accordance with a more limited aspect of the present invention, the method further includes notifying registered patients via the communications network when prescriptions are received therefor.

In accordance with a more limited aspect of the present invention, the authentication performed is at least two factor authentication.

In accordance with a more limited aspect of the present invention, prescriptions and orders are not accepted from doctors and patients, respectively, which do not have their identities authenticated.

In accordance with a more limited aspect of the present invention, the identity of at least one of the doctor and the patient is withheld from the pharmacy to which the order is forwarded.

In accordance with another aspect of the present invention, a prescription drug fulfillment system includes a computer connected to a communications network and means for registering doctors, pharmacies and patients as participants such that each registered participant's identity is uniquely defined and determinable. A central database is accessible by the computer and contains accounts created by the registering means for each registered participant. The accounts include identifying data collected by the registering means. Means are provided for authenticating registered participants identities. The authentication means collects authentication data from participants via the communications network and compares it to corresponding data from account records in the central database such that when there is a match the participant providing the authentication data is deemed to be the registered participant to which the account relates. Means are also provided for receiving, via the communications network, prescriptions from authenticated doctors and orders from authenticated patients. Each of the prescriptions indicates a respective registered patient's identity for whom the prescription is intended, and each of the orders indicating the prescription being ordered. Forwarding means forward orders to registered pharmacies via the communications network.

In accordance with a more limited aspect of the present invention, the communications network is the Internet.

In accordance with a more limited aspect of the present invention, the system further includes means for receiving, via the communications network, confirmation from pharmacies to which orders were forwarded. Each of the confirmations indicating that at least one of the following has occurred: the pharmacy has received the order, the pharmacy has accepted the order, the pharmacy is filling the order or the pharmacy has completed filling the order.

In accordance with a more limited aspect of the present invention, the system further includes means for forwarding, via the communications network, the received confirmations to at least one of the patient from which the corresponding order was received and the doctor from which the correspond prescription was received.

In accordance with a more limited aspect of the present invention, the system further includes means for notifying registered patients via the communications network when prescriptions are received therefor.

In accordance with a more limited aspect of the present invention, the authentication means employs at least two factor authentication.

In accordance with a more limited aspect of the present invention, the means for receiving prescriptions and orders does not accept prescriptions and orders from doctors and patients, respectively, which do not have their identities authenticated.

In accordance with a more limited aspect of the present invention, the means for forwarding orders withholds at least one of the doctor's identity and the patient's identity from the pharmacy to which the order is forwarded.

In accordance with another aspect of the present invention, a method of regulating access via a communications network to medical/pharmaceutical data maintained by a record holder having a presence on the communications network includes providing access controls which are selectively set by an account holder. The account holder has medical/pharmaceutical data related thereto maintained by the record holder, and the access controls specify a level of authorization to be granted to identified requesters seeking access to medical/pharmaceutical data. The method also includes receiving, via the communications network, a contact from a requester seeking access to the medical/pharmaceutical data maintained by the record holder and authenticating the requestor's identity. The identified requestor is granted the specified level of authorization determined from the access controls.

In accordance with a more limited aspect of the present invention, the provided access controls specify the level of authorization to be granted to a whole class of requesters.

In accordance with a more limited aspect of the present invention, a determined level of authorization permits a requestor to carry out at least one of the following: writing prescriptions for the account holder, ordering prescriptions for the account holder, filling a prescription for the account holder, receiving the medical/pharmaceutical data from the record holder, and modifying the medical/pharmaceutical data maintained by the record holder.

In accordance with a more limited aspect of the present invention, the identity of the requestor is not revealed to the record holder.

One advantage of the present invention is that access to and communication of confidential medical and/or pharmaceutical records is privately, securely and readily carried out.

Another advantage of the present invention is that participants are protected from fraudulent or otherwise unauthorized access to confidential medical and/or pharmaceutical records.

Yet another advantage of the present invention is that a prescription drug recipient and/or patient may have a prescription expeditiously fill at their pharmacy of choice without the prescribing doctor having to know the patient's choice of pharmacy.

Still further advantages and benefits of the present invention will become apparent to those of ordinary skill in the art upon reading and understanding the following detailed description of the preferred embodiments.

BRIEF DESCRIPTION OF THE DRAWING(S)

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENT(S)

Figure 1:
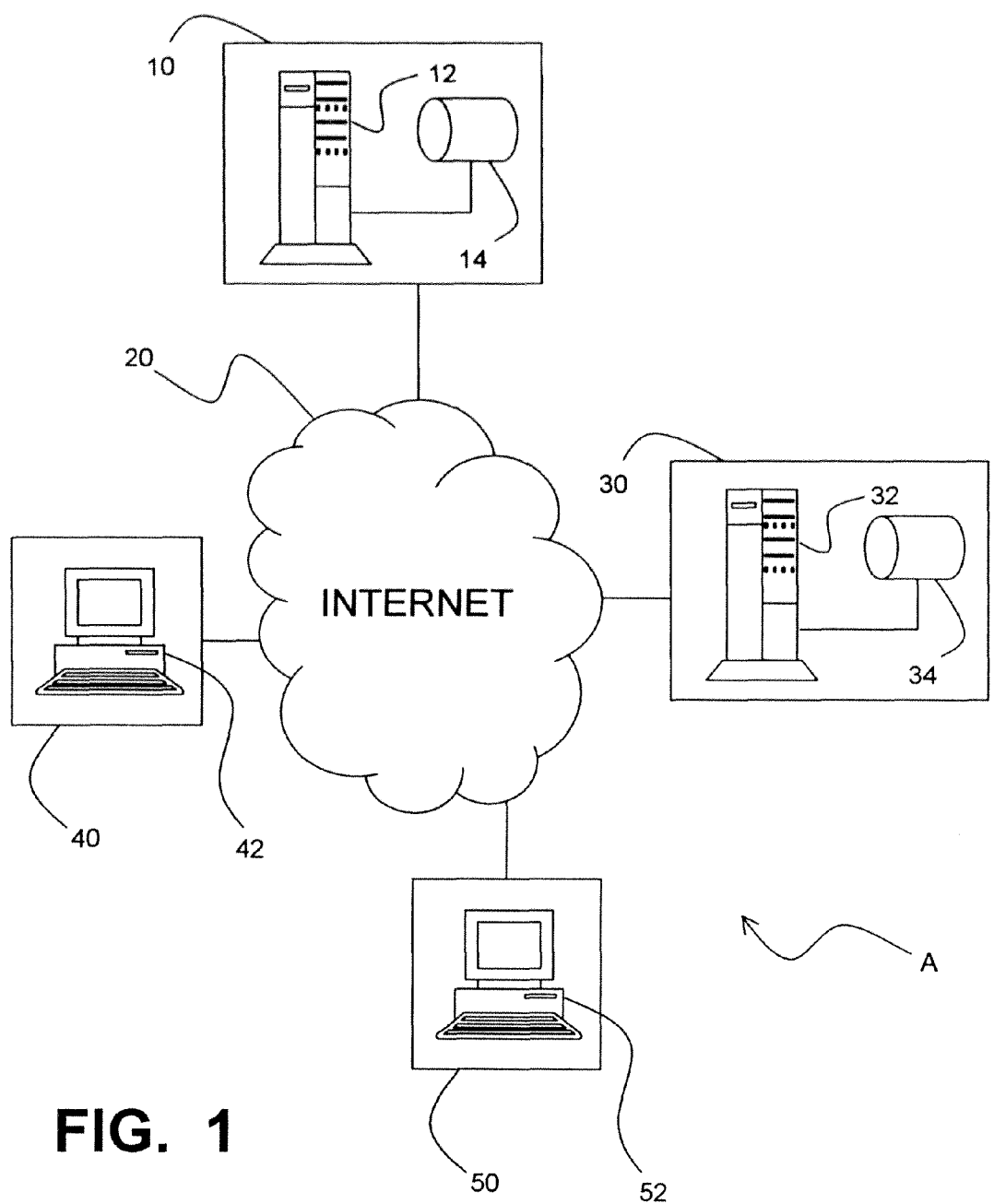
FIG. 1 is a block diagram showing an authentication system for pharmaceutical prescription fulfillment and data access in accordance with aspects of the present invention for use in connection with a communications network.

In accordance with aspects of a preferred embodiment of the present invention, FIG. 1 shows an authentication system A for fulfilling drug prescription processing. The system A includes an authenticating agent 10 which maintains a presence on the Internet 20 or other like communications network via a server 12 or otherwise. A prescription drug provider 30 (e.g., a pharmacy or the like) also maintains a presence on the Internet 20 via a server 32 or otherwise. A prescription originator or writer 40 (e.g., a medical facility, a doctor, physician or other health care professional, a hospital, etc.) gains access to the Internet 20 using a computer 42 with an appropriate web browser or other like software running thereon. Similarly, a prescription drug recipient or patient 50 gains access to the Internet 20 using a computer 52 with an appropriate web browser or other like software running thereon. Of course, the system A is preferably administered to multiple similarly situated pharmacies 30, doctors 40, and patients 50. However, in the interest of simplicity herein, only one of each is shown in FIG. 1. Moreover, while described herein with reference to the Internet 20, upon reading and understanding the present content it will be appreciated by those of ordinary skill in the art that other communications networks, local or wide area computer networks, cellular networks, hard wired networks, etc., may also be employed as the means for communicating data and/or information between participants. Likewise, various terminals or other desired interfacing hardware optionally replaces the computers and servers as appropriate for a given network. Additionally, while not explicitly proposed in every instance described herein, it is to be appreciated that security of the system A is further enhanced by optionally encrypting, with known encryption techniques, any or all of the communications relayed or otherwise transmitted over the Internet 20.

Note, as used herein participants refers to any one or more of the aforementioned pharmacies 30, doctors 40 or patients 50. Likewise, pharmacies 30 refers generally to prescription drug providers, doctors 40 refers generally to medical care givers, medical facilities and the like which write prescriptions or order prescription drugs for patients, and patients 50 refers generally to prescription drug takers or recipients.

Each pharmacy 30 also preferably maintains a database 34. The respective databases 34 contain personal and/or confidential pharmaceutical records, data or information related to patients or prescription drug recipients 50 which are patrons of, or otherwise serviced by, the pharmacy 30. For example, the pharmaceutical records maintained by the pharmacy 30 in their database 34 may contain, without limitation: the patient's name, address, social security number, age, sex, weight and/or other like personal information, a list of known or reported medical conditions which may be impacted by prescription drugs, a list of outstanding prescriptions filled by the pharmacy for the patient, a prescription history for the patient, a list of known or reported drug allergies for the patient, a list of the patient's doctors, medical care givers and/or drug prescribers, a list of prohibit drugs for the patient, an indication of the patient's preference for generic or name brand drugs, data related to the patient's insurance coverage, data related to the patient's preferred form(s) of payment, etc.

Figure 2:
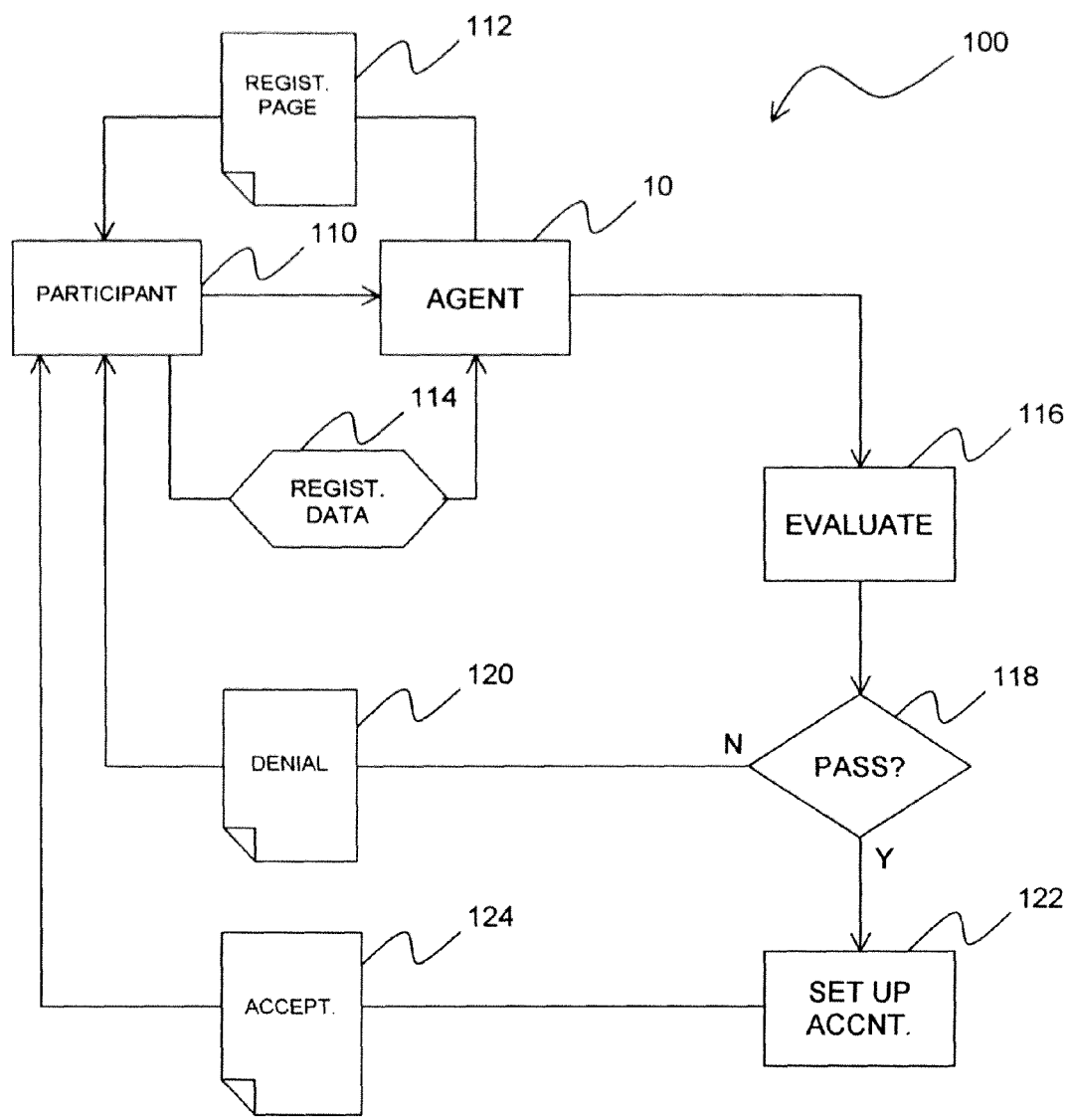
FIG. 2 is a block diagram showing an exemplary participant registration process in accordance with aspects of the present invention.

With additional reference to FIG. 2, a registration process 100 is administered by the authenticating agent 10 to prospective participants 110, preferably, over the Internet 20. Once registered, the participant 110 becomes part of and/or may utilize the system A.

Registration is carried out such that each participants' identity is uniquely defined and determinable. In one preferred embodiment, the registration of a participant 110 begins with a visit by the participant 110 to the authenticating agent 10. Over the Internet 20, the interested participant 110 using an appropriate web browser accesses or is otherwise provided a registration page 112 which is made available via the agent's sever 12. As the registration process 100 continues, registration data 114 is collected or otherwise obtained by the agent 10 from the potential new participant 110 which is making application for participation in the system A. The registration data 114 may include, e.g., in the case of patients or drug recipients 50, their name, age (date of birth), sex, weight, social security number, and/or other like personal information, address, e-mail address, home phone number, work phone number, mother's maiden name, employer, a list of known or reported medical conditions which may be impacted by prescription drugs, a prescription history for the patient, a list of known or reported drug allergies for the patient, a list of the patient's doctors, medical care givers and/or drug prescribers, a list of prohibit drugs for the patient, an indication of the patient's preference for generic or name brand drugs, data related to the patient's insurance coverage, data related to the patient's preferred form(s) of payment, etc.; and in the case of prescription orders or writers 40 and/or prescription drug providers 30, the nature of the participant (i.e., medical facility, doctor, hospital, physician, pharmacy, etc.), their name, address, phone number, tax ID numbers, identification of their medical or pharmaceutical credentials or licenses, e-mail and/or web address, etc.

Prior to accepting a new participant 110, the participant 110 is evaluated by the agent 10. Preferably, the evaluation process 116 verifies the participant's identity from the collected registration data 114 and determines the user's qualifications for participation, including optionally determining patients' credit worthiness. Optionally, the collected data 114 is used to verify the participant's identity by determining its consistency with information made available from conventional identity verification sources. To retrieve the information from the conventional identity verification sources, the agent 10 preferably obtains consent from the participant 110 to access the same when the registration data 114 is collected.

When the participant 110 intends to process payments for commercial transactions using the system A (e.g., when a patient 50 intends to purchase prescription drugs from a pharmacy 30 using the system A), the participant's credit worthiness is preferably evaluated. In determining credit worthiness, the agent 10 optionally passes relevant user registration data to an appropriate financial institution or credit bureau where it is analyzed for credit worthiness. Alternately, the data is analyzed by the agent's own credit approval system. The analysis preferably includes the application of known credit approval techniques and algorithms which determine credit worthiness. Alternately, one or more, new or previously existing debit or credit accounts are set up for the patient 50 based on the analysis and/or the financial data obtained.

For doctors 40 and pharmacies 30, the evaluation preferably includes a verification of their credentials and/or licenses. To achieve the foregoing verification, the collected registration data 114 is compared to corresponding data made available from the government office or agency which issues the credentials and/or grants the licenses. Where the government office or agency is on-line, the verification of credentials and/or licenses is preferably carried out automatically over the Internet 20.

Additionally, the doctors and/or pharmacies are evaluated to determine compatibility of their practices with the system A. For example, it is optionally determined if the pharmacies 30 maintain suitably reliable records, and if the records are maintained in an accessible manner and/or in a compatible database. Additionally, the doctors' and/or pharmacies' general business practices may be subjectively and/or objectively evaluated and their participation denied to insulate patients 50 from those participants with poor customer or patient relations/satisfaction or other potentially undesirable traits.

Upon completion of the evaluation process 116, the agent 10 decides, at decision step 118, if the potential new participant 110 has passed or failed the evaluation. If the participant 110 has failed the evaluation, they are so notified via an application denial 120 being send to them, preferably, electronically from the agent's server 12, e.g., in the form of a web page or an e-mail message. Once the denial has been sent the registration process 100 ends. Alternately, the participant 110 is given the option to change or correct the registration data 114, and resubmit it. However, the number of resubmissions is preferably limited.

On the other hand, if the participant 110 passes the evaluation, then an appropriate account is opened 122 and the participant 110 notified of the outcome via an application acceptance 124 being sent to the participant 110, again, preferably, electronically from the agent's server 12, e.g., in the form of a web page or an e-mail message. The application acceptance 124 preferably includes information related to the created account including, e.g., an account number or an assigned or selected user ID or name, a list of any limits or restriction placed on the account by the participant 110 or agent 10, and/or other related data, optionally, including confirmation of the submitted registration data 114.

The created account and data or information related thereto (e.g., the associated registration data 114) is preferably maintained by the agent 10 in its database 14 along with the accounts for other registered participants.

In another preferred embodiment, the participants 110 does not directly register with the agent 10. Rather, the registration data 114 is collected for the agent 10 by a trusted representative which in turn conveys it to the agent 10, optionally, in batch form. For example, the trusted representative may be a previously registered participant that independently signs up other participants for the system A. For example, pharmacies 30 may sign up doctors 40 and/or patients 50 who are their patrons, doctors 40 may sign up their patients 50, etc. In any event, the registration process is essentially the same as shown in FIG. 2 with the trusted representative taking the place of the participant 110.

In conjunction with the account creation, an authentication vehicle is preferably set up for the doctors 40 and patients 50 (collectively referred to herein as users). The authentication vehicle is preferably two factor authentication. However, authentication using more or less factors is contemplated depending on the level of security desired. In a preferred embodiment, the authentication vehicle is a dynamically changing password implemented via a hardware token issued to the user, a software object loaded on the user's computer or some combination of both. Alternately, the dynamically changing password is generated by an algorithm which is synchronized to a clock or it is sequentially selected from a limited pre-generated list of random or quasi-random values. In still other contemplated embodiments, other secure authentication vehicles and/or techniques may be employed, e.g., challenge response, quick log mode, other one or more factor authentication methods such as a static username and password or pin number, smart cards, or biometric authentication such as fingerprint recognition and retinal scanners etc. To varying degrees, these authentication techniques all enable the agent 10 to positively identify users of the system A.

Preferably, in the case of pharmacies 30, once acceptance has been finalized, the agent 10 forwards a participation kit to the pharmacy 30 enabling the pharmacy 30 to participate in the system A. On-line, the kit is preferably forwarded via the Internet 20. The participation kit outlines the rights and responsibilities or duties of the pharmacy 30 with respect to their participation in the system A. Optionally, the kit includes a participation agreement and a software object for installation on the pharmacy's server 32. After the pharmacy 30 signs the agreement physically, electronically or otherwise, it is returned to the agent 10, perhaps through the agent's server 12. Upon receipt of the signed agreement, the agent 10 maintains the agreement in its database 14, e.g., along with the pharmacy's account information or records.

The software object acts to interface the pharmacy's server 32 with the system A. Optionally, the software object is functional to recognize pre-authenticated users directed to the pharmacy's server 32 from the agent's server 12. In another embodiment, the software object automatically routes users directly accessing the pharmacy's server 32 to the agent 10 for authentication, preferably, on the agent's server 12.

Preferably, in the case of all participants, if approved and participation is still desired, the participant supplies the agent 10, along with an indication of their acceptance, additional account creation data. In the case of the users the addition account creation data optionally includes, e.g., a secret personal identification number (PIN), the answers to a number of designated or otherwise selected security questions, designated limits or restrictions on the use of the account, etc. The security questions are preferably questions to which only the user is likely to know the answers (e.g., the account holder's first car, the name of the account holder's dog or the like). The security questions preferably provide an added measure by which to positively identify the user during authentication insomuch as only the true user of the account is likely to know the answers to the questions.

The accounts for users may also contain information or data relating to account privileges. In a preferred embodiment, the user has the option to customize or modify their account privileges. The account privileges are customized by the user, for example, by accessing the agent's server 12 over the Internet 20. For security purposes, the user is optionally authenticate as an authorized user of the account, preferably, using the below described authentication procedure, prior to permitting any account modifications. However, at initial account creation, the below described authentication procedure may not be employed. The account privileges are optionally set by the user to limit the use of the account in the system A. That is to say, the set account privileges may restrict the account so that transactions thereon or related thereto are not authorized for specified participants, so that automatically recurring transactions carried out absent the direct participation of the user are not authorized, so that for commercial transactions purchases over a certain price limit are not authorized, and the like.

In a preferred embodiment, the participants may selectively update, customize and/or otherwise modify their accounts as desired. Various account options are preferably made available for them to exercise and their choices are maintained with their account information in the agent's database 14. Consequently, the agent 10 has the information with which to regulate account usage in accordance with the desires of the registered participants.

Figure 3:
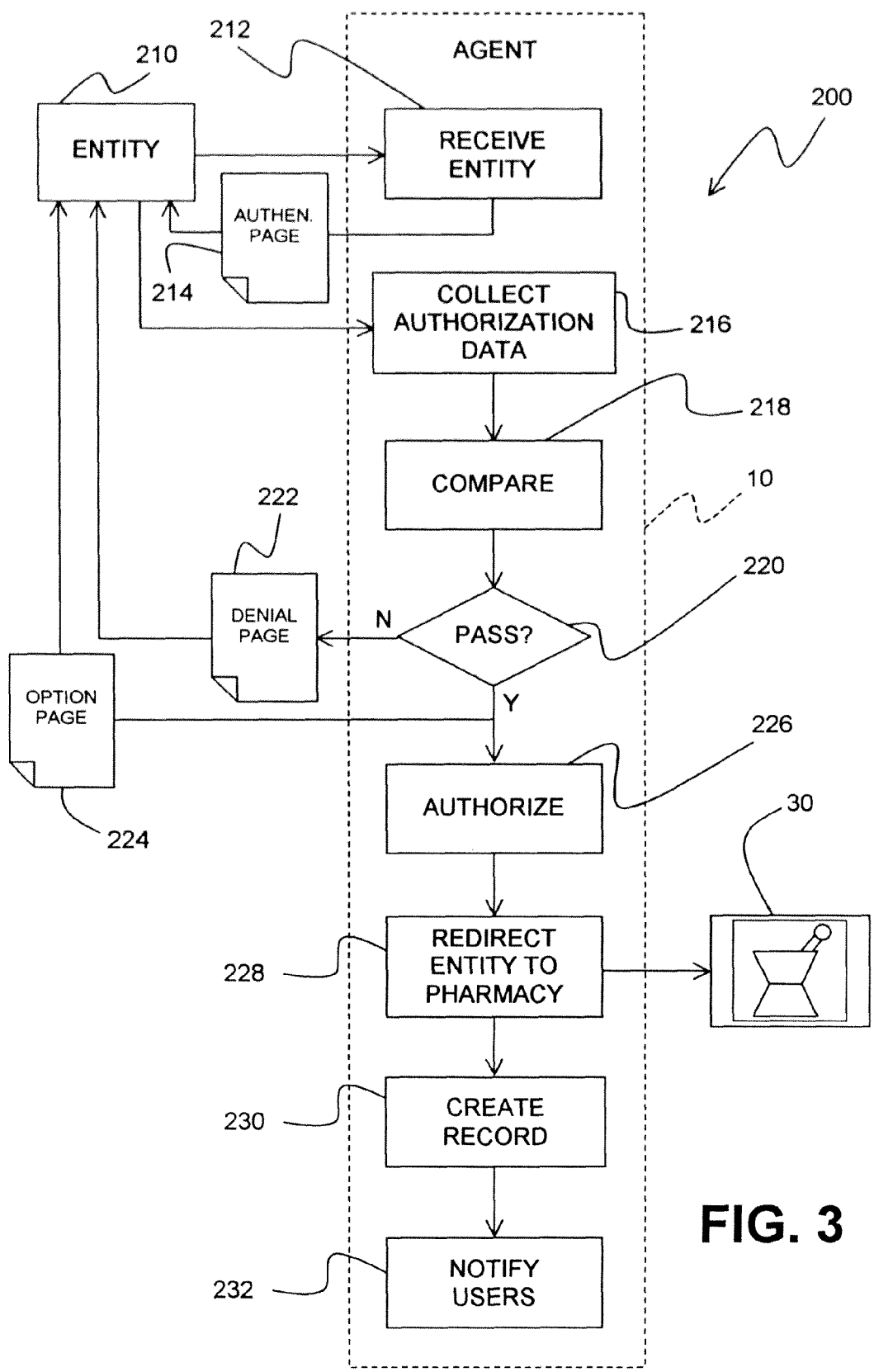
FIG. 3 is a block diagram showing an exemplary authentication process in accordance with aspects of the present invention.

With additional reference to FIG. 3, an authentication process 200 is shown for positively identifying an otherwise unknown entity 210 which makes contact with the agent 10. The unknown entity 210 may be, e.g., a doctor 40 or patient 50 or other party which the agent 10 is to authenticate. At step 212, the agent 10 receives contact from the unknown entity 210, preferably, via the Internet 20. This prompts the agent's server 12 to provide an authentication page 214 to the unknown entity 210. The authentication page 214 is designed to filled in which authentication data. Depending of the authentication vehicle, the authentication data may include a user name or ID, a secret password, a dynamically changing password, a PIN, answers to security questions, biometric data, etc. The authentication data is filled in and submitted by the unknown entity 210. Upon submission of the completed authentication page 214, the authentication data is collected by the agent 10 at step 216. At step 218, the authentication data collected by the agent 10 is compared for consistency to the account information maintained in the agent's database 14, and where there is a match the entity is deemed authentic and positively identified as the holder of the matching account, i.e., the corresponding registered user or participant. Next, at decision step 220, if the entity fails to pass authentication a denial page 222 is provided thereto and the process 200 ends. Optionally, the denial page 222 permits the unknown entity 210 to change and/or correct previously misentered authentication data and try again. The number of tries is, however, preferably limited. On the other hand, if the entity passes authentication an option page 224 is provided thereto. The option page 224 presents the now identified registered user or participant with selected or predetermined options for authenticated parties. The entity is then free to proceed as an authenticated positively identified registered user or participant. Preferably, the options are customized for the identified participant. For example, doctors 40 may be presented with the options of posting prescriptions, modifying or canceling previously posted prescriptions, accessing pharmaceutical records, modifying their accounts etc., and patients 50 may be presented with the options of ordering prescriptions, accessing their pharmaceutical records, modifying their accounts, etc.

In another preferred embodiment, the unknown entity 210 may have contacted a registered pharmacy 30 directly and was merely referred to the agent 10 solely for the purposes of authentication and optional authorization (step 226) prior to completion of their interaction (i.e., before the delivery of requested information, granting of desired access or carrying out of selected commercial transactions). The process 200 is accordingly administered by the agent 10 and the entity redirected back to the referring pharmacy 30. More specifically, completion of the interaction is optionally initiated by the as of yet unknown entity 210 selecting or otherwise activating a link on a check-out or execution page provided by the pharmacy 30. The link is optionally associated with the software object installed on the pharmacy's server 32, i.e., the software object that came with the pharmacy's registration kit. The link and/or associated software object redirects the unknown entity 210 to the agent's server 12 for authentication and optional authorization. Thereafter, the authentication process 200 is carried out. However, at its conclusion, rather than providing the option page 224, the agent 10 redirects the entity, at step 228, back to the referring pharmacy 30, preferably, along with an indication of the authentication results and/or the entity's identity. At that point, the pharmacy 30 and/or entity may interact as they see fit without further involvement by the agent 10. Nevertheless, the pharmacy 30 is made aware of the entity's authenticity and/or identity prior to completion of a commercial transaction (i.e., purchasing of pharmaceuticals), or forwarding of, and/or granting access to, pharmaceutical records, etc. In this manner, the pharmacy 30 has confirmed reliable information regarding the authenticity and/or identity of the entity they are dealing with and may act accordingly.

Optionally, the agent 10 also determines at step 226 the now identified entity's level of authorization. Selected and/or requested authorization data is then returned to the pharmacy 30, along with the redirected entity. Alternately, the selected authorization data to be sent and/or the desired format thereof is predefined in the pharmacy's account, or it is individually requested and/or defined when the entity is directed to the agent 10 by the pharmacy 30. The authorization data optionally indicates a level of authorization set for the identified user. The level may have been set by the user or pharmacy 30 upon registration or upon subsequent modification of the respective participant accounts maintained by the agent 10. The indicated level returned to the pharmacy 30 preferably informs the pharmacy 30 of the degree of access to be granted the user to pharmaceutical data maintained by the pharmacy 30, the privileges granted to the user (i.e., to write prescriptions, to order prescriptions, etc.), the dollar amount which the user is authorized to spend in a given commercial transaction, etc.

In one preferred embodiment, the user's identity is withheld from the pharmacy 30. In this manner, the users maintain their privacy while the pharmacies 30 are assured by the agent 10 that the users are authorized for the contemplated transaction or to access the information being requested. This privacy aspect is optionally implemented in any of the embodiments described herein where the agent 10 is responsible for both the authentication and optional authorization. By relying on the agent 10 to fulfill both these functions, the pharmacies 30 can carry out their end of a transaction or interaction without knowing the actual identity of the user. All the pharmacy 30 has to know is that the user is in fact authentic and authorized to perform the contemplated interaction.

The process 200 preferably continues, at step 230, with the creation of a record memorializing the same. That is, once the authentication and/or authorization has been processed or simultaneously therewith, the agent 10 creates a record of the transaction and maintains the same in its database 14. The record is optionally stored with one or more of the respective participants' accounts. The transaction record preferably contains data related to the transaction such that the details of a particular transaction may be review for tracking purposes if desired to determine what actions took place or the current status of processing. For example, the transaction record optionally contains the identity of the user or participant involved, the results of the authentication and/or authorization, the actions taken or information accessed, the date and time of the transaction, a unique transaction identifier or authorization number, etc. In this manner, transaction details are preserved such that any potential future discrepancies may readily be resolved.

In a preferred embodiment, the agent 10 also conducts an independent notification procedure 232 wherein participants are independently notified of agent activities. Preferably, independent confirmation that an authentication or authorization has been requested and/or that the processing of the same has been completed is sent to all the participants. Optionally, the notification is automatically forwarded to the respective e-mail addresses on file for the participants in the agent's database 14. The notification preferably includes the data from the record generated in step 230.

Additionally, via the notification procedure 232, the agent 10 preferably independently notifies a registered user when an authentication or authorization attempt fails. The failure notification is preferably forwarded to the e-mail address on file for the user in the agent's database 14. In this manner, a true user is made aware of an attempted use of their account by an imposter.

Figure 4:
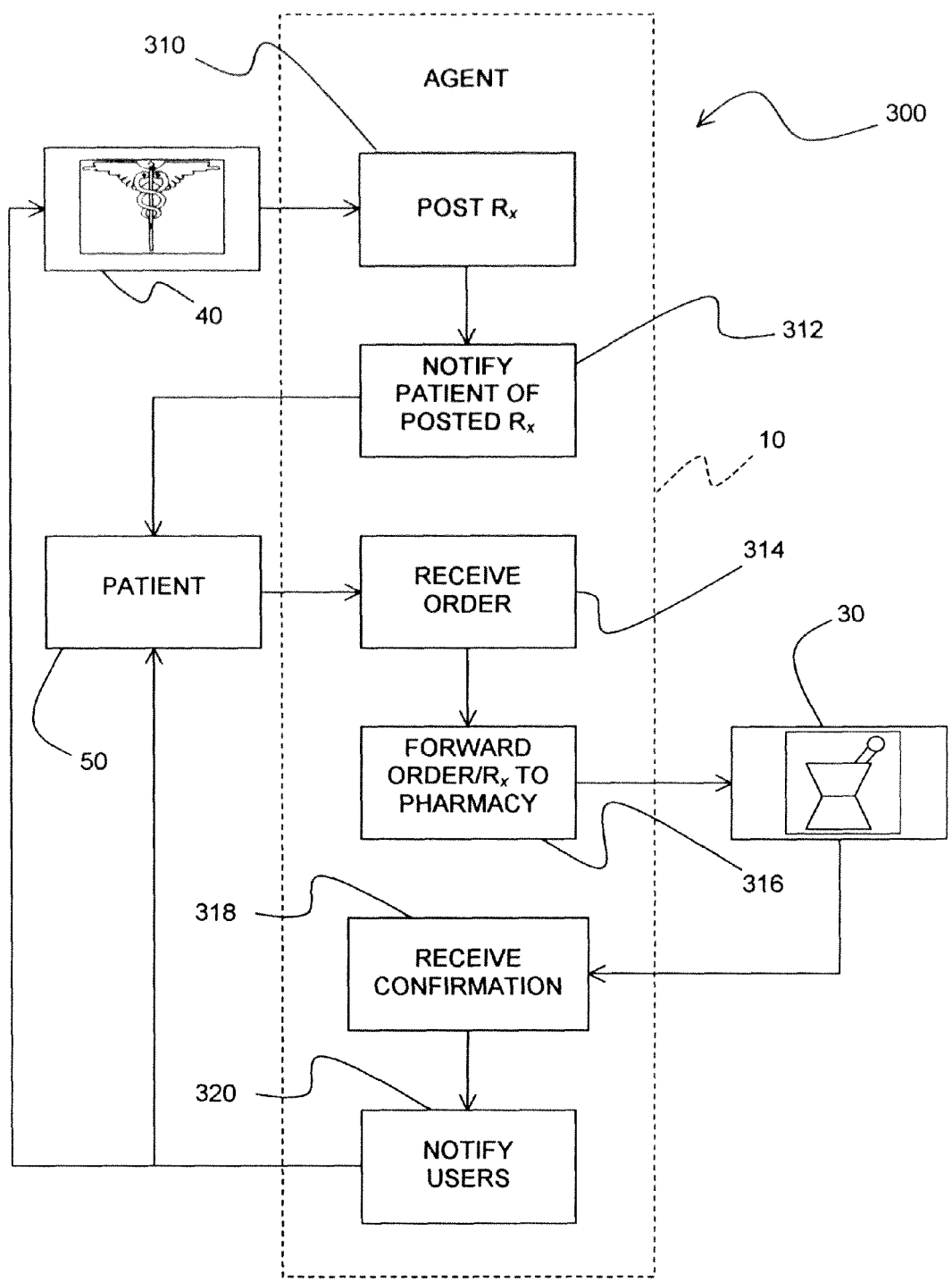
FIG. 4 is a block diagram showing an exemplary prescription fulfillment process in accordance with aspects of the present invention.

By way of example, FIG. 4 shows a prescription fulfillment process 300 carried out over the Internet 20 in accordance with a preferred embodiment and/or aspects of the present invention. The process 300 preferably begins with a registered doctor 40 contacting the agent 10. Once the doctor 40 is authenticated and/or authorized by the agent 10, a prescription is posted at step 310. Prescription posting is achieved by the agent 10 collecting or otherwise receiving relevant prescription data (e.g., an identification of the drug being prescribed, the dosage, the number and/or frequency of refills, a date when the prescription expires, the name or identity of the registered patient for which the prescription is intended, instructions for taking the drug, restrictions on and/or instructions for filling the prescription, etc.) from the doctor 40. In a preferred embodiment, the prescription data is collected via a web page which is provided to the doctor 40 who fills it in and submits it back to the agent 10. The agent 10 maintains the prescription data in an associated record in the database 14. Optionally, a unique prescription ID is assigned to the prescription record. Preferably, the posted prescription is correlated with the corresponding patient account maintained by the agent 10 in the database 14. In addition, the prescription preferably remains accessible to the doctor 40 so that, as desired, future changes can be made thereto or the prescription may be canceled altogether.

At step 312, the registered patient 50 for which a prescription was posted is notified by the agent 10 of the posting. In a preferred embodiment, the agent 10 e-mails the prescription data and ID from the prescription record to the patient 50. In this manner, the patient 50 is made aware of the prescription's posting and may act accordingly. Optionally, the patient 50 may actively seek a prescription posting by accessing their account with the agent 10. In either case, once the patient 50 has been authenticated and/or authorized by the agent 10, they may selectively order a posted prescriptions. At step 314, prescription ordering is achieved by the agent 10 collecting or otherwise receiving relevant order data (e.g., the prescription ID of the prescription being ordered, the registered pharmacy at which the patient wishes to have the prescription filled, payment data, insurance data, delivery instructions, etc.) from the patient 50. In a preferred embodiment, the order data is collected via a web page which is provided to the patient 40 who fills it in and submits it back to the agent 10. The agent 10 maintains the order data in an associated record in the database 14. Optionally, a unique order ID is assigned to the order record. Preferably, the order is correlated with the corresponding pharmacy account maintained by the agent 10 in the database 14. At step 316, the agent 10 forwards the order data to the designated registered pharmacy 30 in the order record, along with the prescription data from the identified prescription.

The pharmacy 30 preferably acknowledges receipt of the ordered prescription, fills the prescription and delivers it in accordance with the prescription and order data received. Upon completion of or simultaneously with each of the aforementioned acts, the pharmacy 30 returns confirmation data to the agent 10 confirming the same. The confirmation data is received by the agent 10 at step 318 and an associated record is created and/or maintained in the database 14. At step 320, the involved users are notified of the pharmacy's actions, e.g., by forwarding of the confirmation data to the users.

In a preferred embodiment, participants may selectively place access controls on their accounts, set account privileges or set defaults to customize their respective accounts. The account controls and/or privileges are used by the agent 10 to determine the appropriate authorizations granted to authenticated participant. For example, a patient 50 may designate their account so that only specified doctors 40 may post prescriptions for them. Accordingly, if an unspecified doctor 40 attempts to post a prescription for a patient 50 they are denied authorization and the prescription is not posted. Similarly, the patient 50 may designate a default pharmacy 30 to fill ordered prescriptions. Accordingly, when a prescription is ordered, it is automatically forwarded to the default pharmacy unless the patient 50 indicates otherwise. Other defaults that are optionally chosen by the patient 50 may be a default method of payment or default credit or debit account from which to make payment for ordered prescriptions, a default delivery address and/or default insurance data. Pharmacies 30 may opt to restrict authorization of selected doctors 40 or patient 50. Therefore, ordered prescriptions involving the restricted user are not authorized by the agent 10. Optionally, other instances where orders may not be authorized by the agent 10 include attempts to order expired prescriptions, prescriptions which have already been fill or prescriptions for which no refills remain.

In a preferred embodiment, the agent 10 regulates unauthorized actions by only providing authorized options to the participants. For example, web pages provided to participant to collect data or to present options are limited or custom designed so that only authorized actions may be taken by the participant. Additionally, interest participants are preferably notified of attempted unauthorized actions via a notification process similar to that of step 320. Additionally, notification may be forwarded to interested participants when drugs are prescribed and/or ordered which may have a potentially harmful effect either due to interactions with other prescribed drugs which the patient 50 may be taking or due to the patient's particular circumstances or health. Such information may be readily available from the patient's account maintained by the agent 10 in its database 14. Alternately, the pharmacy 30 filling a particular order may have the information. The patient's account may be selectively customized by the patient 50 so that when such instances arise notification of the same is sent out to interested participants or the appropriate authorizations are automatically denied.

Figure 5:
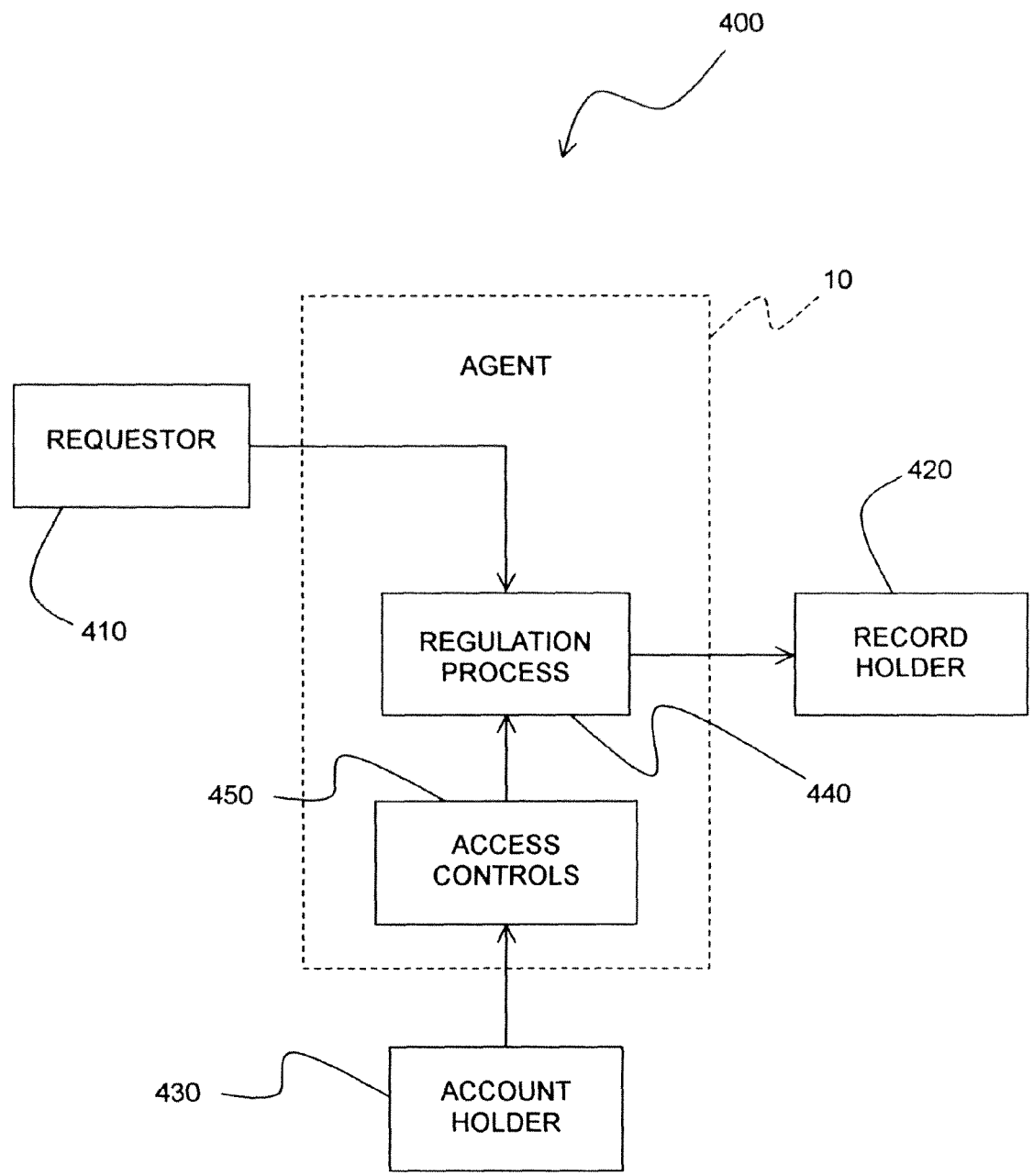
FIG. 5 is a block diagram showing an exemplary data access process in accordance with aspects of the present invention.

With additional reference to FIG. 5, a data access process 400 is shown. Via the data access process 400, the agent 10 authenticates and optionally authorizes a requester 410 seeking access to data maintained by a record holder 420. In this manner, access to confidential and/or personal records is regulated. The data relates to a registered account holder 430, i.e., a patient 50 or participant of the system A. The record holder 430 is preferably a registered doctor 40 or pharmacy 30 which maintains medical or pharmaceutical records of registered patients 50. Optionally, the requestor 410 contacts the agent 10 directly or contacts the record holder 420 directly and is redirected to the agent 10 for authentication and/or authorization. The requestor 410 may be any registered participant (including the account holder himself 430) or a registered interested third party (e.g., an insurance agent or agency) seeking access to an account holder's records.

In a preferred embodiment, the access regulation process 440 is essentially the same as process 200 with the requestor 410 substituting for the user or entity, the record holder 420 substituting for the pharmacy 30 and the transaction or selected interaction being considered access to the records maintained by the record holder 420. That is to say, the option selected is by the requestor 420 or interaction between the requester 410 and record holder 420 involves access to the records or data of interest. Depending on the degree or level of authorization granted to the requester 410, access to the records may amount to the communication of selected data to the requestor 410 or may permit the requester 410 to modify or update selected records.

In the access process 400, access controls 450 are preferably set by the account holder 430. The access controls 450 define the level of access and/or authorization granted to requesters 410 via the regulation process 440. They may control the extent of the access granted or the number of times access is granted. The data reflecting predefined access controls 450 is preferably maintained by the agent 10 in its database 14 along with the account to which they relate. The predefined access controls 450 are set at the time of the account's creation or subsequent modification.

The access controls 450 may regulate access based on the particular requestor 410 or may regulate access for a whole class of requesters 450. For example, the access controls 450 may be set so that when the requester 410 is identified by the agent 10 as the account holder 430 himself, unfettered access and/or authorization is granted. In another example, the access controls 450 may be set so that that when the requestor 410 is identified by the agent 10 as a specified doctor 40 or pharmacy 30 a desired level of access or authorization is granted. In selected instances, access may be limited to a one time access. For example, the access controls 450 may be set so that when the requester 410 is identified by the agent 10 as a specified insurance agent or agency, access or authorization is granted, but only once. Optionally, the access controls 450 may be set so that when the requester 410 is not identifiable by the agent 10 no access or authorization is granted.

With respect to classes of requesters 410, a desired level of access or authorization may be granted when the agent 10 identifies the requester 410 as belonging to a defined class. This can be particularly useful when the requester 410 belongs to a defined class such as emergency room doctors or facilities. While the particular requester 410 may not have been expressly specified beforehand as authorized by the account holder 430, due to the exigency of the situation the account holder 430 may nevertheless desire that access or authorization be granted to their medical and/or pharmaceutical records.

Optionally, the access controls 450 may set on a per-request basis. That is to say, when an otherwise unauthorized access is attempted by a requestor 410, the corresponding account holder 430 is notified (e.g., via e-mail or otherwise) and given the opportunity to allow, deny or otherwise restrict the level of access granted to the particular requestor 410. In this instance, the notification preferably includes any information the agent 10 is able to discern regarding the requestor 410 so that the account holder 430 can make an informed decision. Preferably, the otherwise unauthorized requestor's access is delayed or put on hold until the account holder 410 responses or until a set time period has elapsed at which time access is automatically denied.

Preferably, the process and/or procedure carried out by the agent 10 as described above are implements via software, computer programs or the like running on the agent's server 12, via hardware connected to the agent's server 12 or via a combination thereof.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A computer-implemented method of processing drug prescriptions via the Internet, wherein the method is performed by a pharmacy registered with an external agent, said method comprising:
 a) receiving a first request at a server and over the Internet, wherein the first request is received from a doctor registered with the external agent and specifies a prescription, wherein the prescription identifies a patient registered with the external agent;
 b) redirecting the doctor to the external agent via the server and using the Internet, wherein the external agent authenticates the doctor and returns the doctor using the Internet;
 c) receiving a second request at the server and over the Internet, wherein the second request is received from the patient registered with the external agent and specifies an order for the prescription;
 d) redirecting the patient to the external agent via the server and using the Internet, wherein the external agent authenticates the patient and returns the patient using the Internet;
 e) receiving a patient authorization level from the external agent at the server, wherein the authorization level limits a dollar amount which the patient may spend on one order; and,
 f) the server rejecting the second request when the second request exceeds the patient authorization level and allowing the second request when the second request does not exceed the patient authorization level.

2. The method of claim 1, wherein the first request and/or the second request are sent by the doctor and/or the patient, respectively, using a computer program.

3. The method of claim 1, wherein the external agent further determines a doctor authorization level, said method further comprising:
 e) receiving the doctor authorization level from the external agent; and,
 f) rejecting the first request if the first request violates the doctor authorization level.

4. The method of claim 3, wherein the authorization level includes one or more limitations on requests from the doctor.

5. The method of claim 4, where the limitations include a limit on which patients the doctor may submit prescriptions for.

6. The method of claim 4, wherein at least one of the limitations is set by a patient.

7. The method of claim 1, wherein the authorization level is set by the patient.

8. The method of claim 1, further comprising:
e) notifying the patient of receipt of the prescription.

9. A computer-implemented method of processing drug prescriptions comprising:
a) registering with an external agent one or more doctors, one or more pharmacies, and one or more patients as users of a common Internet based system, wherein each of the registered users include a unique system user identity, wherein the external agent comprises a server;
b) receiving a plurality of prescriptions by the common Internet based system from doctors registered as users, wherein the prescriptions are written for patients registered as users;
c) posting received prescriptions in a database of the common Internet based system prior to pharmacy selection by patients registered as users;
d) choosing pharmacies registered as users to fill the plurality of posted prescriptions by patients registered as users for whom the prescriptions are posted, wherein each prescription to be filled by a chosen pharmacy for a specific patient comprises an order;
e) determining a patient authorization level for at least one of the patients, wherein the authorization level limits a dollar amount which a given patient may spend on one order;
f) rejecting an order for the given patient when the order exceeds the patient authorization level and allowing an order for the given patient when the order does not exceed the patient authorization level; and
g.) forwarding the allowed orders from the common Internet based system to the chosen pharmacies registered as users.

10. The method of claim 9, wherein receiving from doctors registered as users prescriptions for patients registered as users is based on account controls and/or privileges set by at least one of the patients registered as a user and for whom the prescription is written.

11. The method of claim 9, wherein choosing one or more registered users which includes pharmacies is limited based on account controls and/or privileges set by at least one of the patients.

12. The method of claim 9, further comprising:
notifying a registered user which includes patients of receipt of a prescription written for that registered user.

13. The method of claim 12, wherein the notification comprises an email message.

14. The method of claim 9, further comprising:
receiving by the common Internet based system a confirmation from at least one of the pharmacies registered as a user, wherein said confirmation indicates at least one of the following has occurred:
the pharmacy has received the order,
the pharmacy has accepted the order,
the pharmacy is filling the order, and
the pharmacy has completed filling the order.

15. The method of claim 14, further comprising:
forwarding the confirmation to at least one of:
at least one of the patients registered as a user, and
at least one of the doctors registered as a user.

16. The method of claim 9, further comprising:
authenticating a registered user identified by a unique system user identifier to the common Internet based system which is performed using a dynamically changing password.

17. The method of claim 9, wherein choosing automatically defaults to a specific pharmacy pre-selected by at least one patient registered as a user.

18. The method of claim 9, wherein at least one order forwarded excludes at least one of:
the identity of the doctor who wrote the prescription; and
the identity of the patient.

19. The method of claim 9, wherein choosing includes:
comparing prices of filling an order from more than one pharmacy registered as a user.

20. The method of claim 9, wherein an account control is placed on the amount charged by pharmacy to fill an order.

21. The method of claim 9, wherein prescriptions written by multiple doctors for one patient and chosen to be filled by one pharmacy comprise an order.

22. The method of claim 9, wherein registering a doctor or a pharmacy as a user further includes:
verifying the credentials and/or licenses of the doctor or the pharmacy with data from government offices which issues the credentials and/or grants the licenses.

23. A prescription drug fulfillment system comprising:
an electronic computer connected to the Internet, said electronic computer comprising:
a registration module that registers one or more doctors, one or more pharmacies, and one or more patients as participants, and provides each registered participant with a unique system user identifier;
a communications module that receives prescriptions from registered doctors over the Internet, receives orders for prescriptions from patients over the Internet for whom the prescriptions were written, and forwards orders to pharmacies over the Internet to whom the orders are designated;
an authentication module that authenticates the registered doctors, the registered pharmacies, and the registered patients using registration data and unique system user identifiers; and,
an authorization module that authorizes the prescription using an authorization level associated with the one of the doctors, wherein the authorization level is based on account controls and/or privileges set by the one of the doctors, and wherein the authorization module further authorizes the order using an authorization level associated with at least one of the patients, wherein the authorization level limits a dollar amount which a given patient may spend on one order, the authorization module operative to reject an order when the order exceeds the patient authorization level and to allow an order when the order does not exceed the patient authorization level.

24. The prescription drug fulfillment system of claim 23, wherein the authorization level of the one of the doctors is based on account controls and/or privileges set by the patients.

25. The prescription drug fulfillment system of claim 23, wherein the authorization module further authorizes the order using an authorization level associated with the one of the patients, wherein the authorization is based on account controls and/or privileges set by the one of the patients.

26. The prescription drug fulfillment system of claim 25, wherein an account control is placed on the amount charged by pharmacy to fill an order.

27. The prescription drug fulfillment system of claim 23, wherein authentication includes:
using a dynamically changing password.

* * * * *